Figure 2:
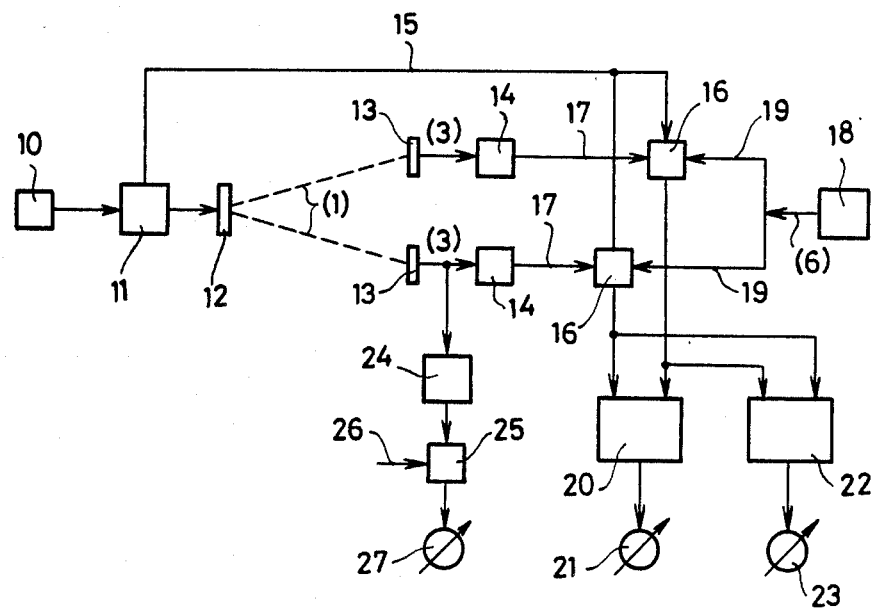

United States Patent [19]

Breeuwer

[11] Patent Number: 4,882,931

[45] Date of Patent: Nov. 28, 1989

[54] METHOD AND AN APPARATUS FOR DETERMINING THE VELOCITY, DIRECTION AND OTHER MAGNITUDES OF A FLOW, IN PARTICULAR A GAS FLOW

[75] Inventor: René Breeuwer, Delft, Netherlands

[73] Assignee: Ahrin BV, Netherlands

[21] Appl. No.: 253,495

[22] Filed: Oct. 5, 1988

Related U.S. Application Data

[63] Continuation of Ser. No. 142,634, Jan. 11, 1988, abandoned, which is a continuation of Ser. No. 912,075, Sep. 25, 1986, abandoned.

[30] Foreign Application Priority Data

Sep. 30, 1985 [NL] Netherlands .......................... 8502673

[51] Int. Cl.$^4$ ........................... G01W 1/04; G01F 1/66
[52] U.S. Cl. ......................................... 73/189; 73/597; 73/861.27
[58] Field of Search ................ 73/189, 861.27, 861.28, 73/861.29, 597

[56] References Cited

U.S. PATENT DOCUMENTS

| | | | |
|---|---|---|---|
| 3,392,574 | 7/1968 | Lemon et al. | 73/861.27 X |
| 4,031,756 | 6/1977 | Rotier et al. | 73/861.27 X |
| 4,112,756 | 9/1978 | MacLennan | 73/861.27 X |
| 4,402,231 | 9/1983 | Ryan | 73/861.27 |

OTHER PUBLICATIONS

Loosemore et al., "A New Ultrasonic Flowmeter", Ultrasonics, Jan. 1969, pp. 43-46.

Primary Examiner—Charles A. Ruehl
Attorney, Agent, or Firm—Beehler & Pavitt

[57] ABSTRACT

A method and an apparatus for determining the velocity, direction and other magnitudes of a flow, in particular a gas flow, in which a strongly damped acoustic signal is emitted by a first transducer in a first direction through the flow towards a second transducer producing a damped electric signal, the first deflection thereof being compared with a threshold value which is lower than the peak value of said deflection, and exceeding said threshold value being used as the end of the time measurement period started at the emission of the acoustic signal by said first transducer. In particular a single first transducer is used, and a reflecting body is placed in front of said first transducer, adapted to reflect the acoustic pulses emitted by said transducer through the flow in different directions towards one or more second transducers.

12 Claims, 2 Drawing Sheets

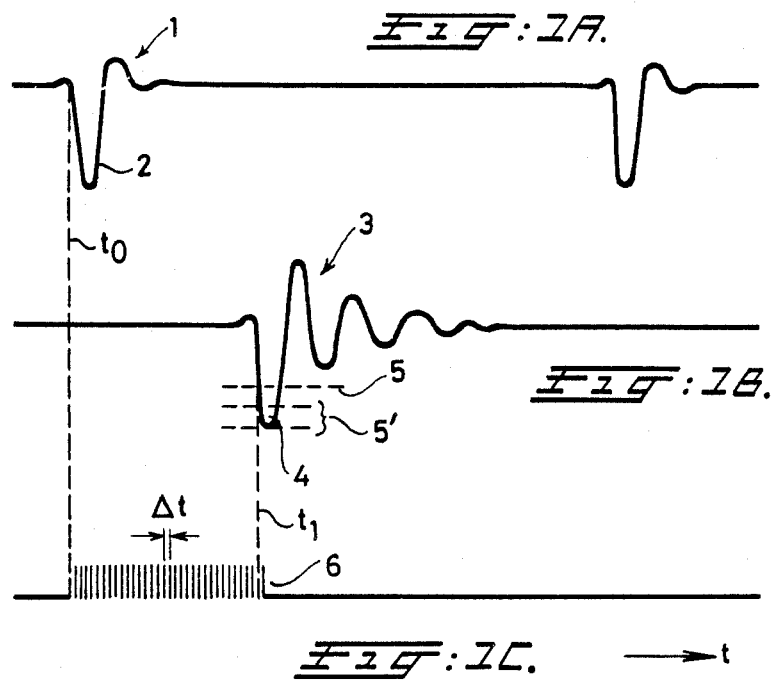
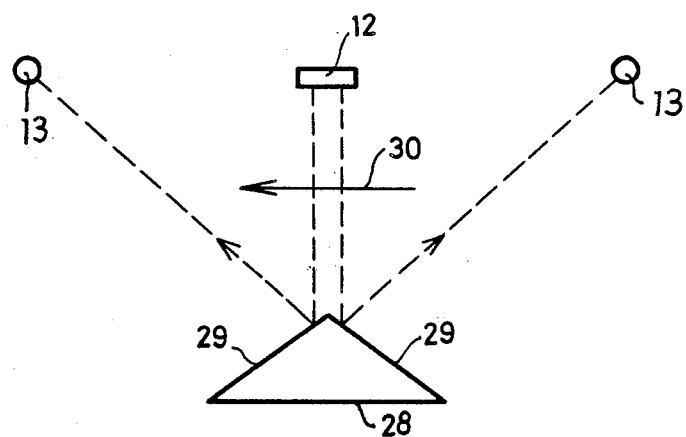

METHOD AND AN APPARATUS FOR DETERMINING THE VELOCITY, DIRECTION AND OTHER MAGNITUDES OF A FLOW, IN PARTICULAR A GAS FLOW

This is continuation application of abandoned U.S. application Ser. No. 07/142,634 filed Jan. 11, 1988, which in turn was a continuation of abandoned U.S. application Ser. No. 06/912,075 filed Sept. 25, 1986, which claimed priority to Netherlands Patent application No. 8502673 filed Sept. 30, 1985.

Measuring the velocity and direction of a flow, in particular a gas flow such as an air flow, and of its temperature and humidity, can be done in different manners. The latter measurements are made by means of other apparatuses than the former ones. In meteorology, for measuring the velocity and direction of air flows, generally apparatuses with moving parts (anemometers and the like) are used, which, because of the inevitable inertia and friction, are not very accurate, will unfavourably influence the flow, and are, moreover, difficultly to be calibrated.

It has already been proposed to determine the velocity and direction of flows by measuring the transit time of acoustic waves in different and in particular opposite directions, but also such measurements are inaccurate, and are, in particular, sensitive for interference and reflection phenomena.

There exists a need for apparatuses for performing such measurements, which apparatuses can operate in an accurate and dependable way, are cheap and not very bulky, and can be maintained in a simple manner.

To that end the invention provides a method for determining the velocity and direction of flow, in particular a gas flow, in which an acoustic signal is directed by means of a first transducer in a first direction through the flow towards a second transducer, which, on reception thereof, produces a corresponding electrical signal, which is also done in a second direction differing from the first one, the transit time of the acoustic signal between the transducers in question being measured by measuring the time lapsed between the emission and the reseption of the acoustic signal, the velocity and direction of the flow being derived from the difference between these transit time measurements, said method being characterised in that the acoustic signal emitted by said first transducer is a strongly damped signal giving rise, in said second transducer, to a dampled alternating voltage, the first deflection of which in one sense having a larger amplitude than the next deflections, said signal being compared with a threshold valve which is lower than the peak value of the first deflection, and exceeding said threshold value being used as the end of the time measurement period, said period being started at the emission of the acoustic signal by the first transducer. In particular a timing pulse counter is enabled when emitting the acoustic pulse, which counter is adapted to count timing pulses produced by an independent source, and being stopped on the reception of the threshold exceeding signal, the emission of acoustic pulses taking place at an arbitrary instant in respect of the fixed timing pulses. The repetition frequency of the acoustic pulses can be substantially lower than the decay frequency of the signal produced by the second transducer, the frequency of the timing pulses being substantially higher than said decay frequency.

Furthermore a plurality of time measurements can be made consecutively, the transit time being determined by a statistical interpolation of the various separate measurements results.

The sum of the transit times in different directions can be used for computing the temperature of the flow, and the attenuation of an acoustic signal can be measured for determining the humidity of a gas flow.

For the latter purpose the first deflection of the signal of the second transducer can be compared with a plurality of threshold values for determining the peak value thereof, and the determined peak value can be compared with a reference value relating to the dry gas.

The apparatus for performing said method, comprising at least a first and a second transducer for emitting and receiving respectively an acoustic signal, and means connected with said transducers for measuring the time lapsed between the emission and reception of the acoustic signal, is characterised in that said first transducer is adapted to emit a strongly damped acoustic signal, in that the second transducer is connected with a threshold circuit having a threshold value which is lower than the first deflection of the electric signal produced by said second transducer, said threshold circuit being adapted to produce a signal when exceeding said threshold, and in that the energising input of said first transducer is connected with the start input of a pulse counter, and the output of said threshold circuit being connected with the stop input of said counter, the counting input of said counter being connected with a source of timing pulses.

In such an apparatus, comprising a plurality of second transducers, adapted to receive acoustic pulses originating from different directions, the means connected therewith for determining the transit time of the acoustic pulses in question can be connected with a summing circuit which is connected with means for computing the temperature of the flow from the sum of transit times.

In particular at least one second transducer is connected with a threshold circuit with different thresholds which is adapted for determining the highest value of the first deflection of the emitted electrical signal, which threshold circuit is connected with a circuit for comparing the determined highest value with a reference value, and for computing therefrom the humidity of the flow.

Such an apparatus can, in particular, comprise a single first transducer and a reflection body positioned in front of said transducer, this in such a manner, that the flow to be examined can flow through the intermediate space, said reflection body being adapted to reflect the acoustic pulses sent by the first transducer through said flow along differently directed paths through said flow towards one or more second transducers.

Said reflection body is, in particular, a trilateral regular pyramid, its apex being directed towards the centre of the first transducer.

Finally the number of transducers can be larger than is required for determining the direction of the flow, means then being present for disabling those transducers which are least favourably positioned in respect of the flow, as well as means for a coarse determination of the flow direction for controlling the first-mentioned means.

The invention will be elucidated below by reference to a drawing, showing in:

FIGS. 1A, B and C representations of waveforms used in an apparatus according to the invention;

FIG. 2 a block diagram of an embodiment of the apparatus according to the invention; and FIG. 3 a diagrammatical representataion of a special arrangement of the piezo-electric transducers of such an apparatus.

FIG. 1A shows an acoustic pulse 1, having a first peak 2 in a given sense, which is shown here as the negative sense, followed by a number of peaks in alternating senses with strongly decresing height. Such a pulse can be produced by discharging a charged capacitor through a piezo-electric transducer. This is repeated with a relatively low frequency, e.g. 500 Hz, so that the interval between successive pulses 1 is larger in respect of the pulse width.

FIG. 1B shows a corresponding representation of the output signal 3 of a piezo-electric transducer on which an acoustic pulse 1 of FIG. 1A is incident. This signal comprises, again, a first peak 4, shown here in the negative sense, as well as a number of subsequent peaks in alternate senses and with decreasing heights. The first peak 4 of the signal 3 has the largest deflection, so that, if only the negative peaks are used for the measurement, the peaks following on the first peak 4 can be excluded by selecting a suitable threshold value 5. By measuring the time lapse between the emission of the emittor pulse 1 and the reception of a signal 3 the transit time can be determined. The interval between the pulses 1 is, then, substantially larger than the duration of the signal 3.

The measurement of the transit time can, for instance, take place by means of clock pulses 6 shown in FIG. 1C. These pulses can, for instance, have a repetition frequency of 10 MHz. The transit time is, then, given by the number of clock pulses 6 counted between the instant $t_0$ at which the pulse 1 was emitted and the instant $t_1$ at which the first peak 4 of the signal 3 exceeds the threshold value 5. As the repetition frequency of the pulses 6 becomes higher, the accuracy of the measurement will be better, but a practical limit is imposed thereon. In practice a frequency of about 10 MHz will be used, so that the time interval $\Delta t$ between two pulses will be about 0,1 $\mu s$.

Another restriction of the accuracy is caused by the fact that as well the enabling instant $t_0$ as the disabling instant $t_1$ of the used counter can be in an arbitrary point between two pulses 6. In order to remove said inaccuracy the measurements will be repeated a sufficient number of times in order to obtain a dependable average. In view of the repetition frequency of the pulses 1, which is, for instance, 500 MHz, dependable statistics can be obtained within a short time.

Even if a subsequent peak of the signal 2 would exceed the threshold value 5, this has no influence on the count, since, at the instant $t_1$, counting is interrupted. Also plural echo signals will not have a noticeable influence on these statistics, since such signal will arrive later and, therefore, will not have an effect, and the distance between the pulses 1 is sufficiently larger for allowing echo signals to decay before a subsequent measurement takes place.

The clock pulses 6 are continuously produced, but the counter used for counting them is enbaled at the instant $t_0$, and is disabled on the instant $t_1$, as the case may be by the intermediary of suitable gates.

The flow velocity can be derives from transit time differences in two different directions, and in particular in opposite directions, and the flow direction can be determined from a plurality of mesurements at different angles.

There exists, moreover, a relationship between the propagation speed of the acoustic waves in a gas and the latter's temperature, which relationship is a substantially linear one. Therefore, also the temperature of the gas can be derived from the verage of a number of transit time measurements if the relationship between the propagation speed and the temperature is known.

The humidity of the gas influences the attenuation of the acoustic pulses in the gas. Said attenuation can be determined by comparing the peak value 4 of the signal 3 with a reference value for dry gas. This peak value can, for instance, be determined by means of a plurality of additional thresholds 5', the just exceeded threshold then substantially corresponding to said peak value. It is also possible to use, to that end, a periodically shifting threshold, which, for instance, is controlled by means of a suitable saw-tooth voltage, and it is also possible that this threshold is a so-called self-learning threshold in that in a series of consecutive measurements the preceding measurement is used as the initial value, so that, again, a dependable average can be determined.

In this manner it becomes possible to measure in a quick and dependable way all the variables of the gas flow to be examined by means of a single apparatus.

FIG. 2 shows a block diagram of an electric circuit suitable for this purpose. This circuit comprises a trigger 10 fixing the repetition period of the pulses 1. This trigger controls a supply circuit 11 for a piezo-electric pulse generator 12 or a plurality of such generators, adapted to emit the acoustic pulses in the desired number of directions; for simplicity's sake only two directions are indicated in FIG. 2, but the number thereof can also be larger or smaller. The acoustic pulses are received by a corresponding number of transducers 13, and are transformed thereby in electric signals 3. The signals 3 are forwarded towards a threshold circuit 14 applying the above-mentioned threshold 5.

On reception of a trigger pulse the circuit 11 causes, for instance, the discharge of a capacitor through the transducer 12, and forwards, moreover, via a line 15 an enabling pulse towards a counter 16 which, on the other hand, can receive via a line 17 a disabling pulse from the associated threshold circuit 14. Moreover each counter 16 receives from a clock pulse source 18 via a line 19 the clock pulses 6, so that in the period between enabling and disabling the counter the received clock pulses can be counted. If necessary means not shown can reset the counters 16 after processing the counts in question.

The outputs of the counters 16 are connected with a processing circuit 20 in which the various transit time measurements are processed for computing the flow velocity and, as the case may be, flow direction of the gase flow to be examined, and the results thereof are displayed on a display apparatus 21.

On the other hand the output signals of the counters 16 are forwarded towards an additional processing circuit 22, which can be a summing circuit, by means of which a result corresponding to the average transit time or a result proportional thereto can be determined, which is a measure for the temperature of the gas, which results can be displayed on an associated display apparatus 23.

Moreover the output signal 3 of one of the transducers 13 can be forwarded to a special threshold circuit 24 by mens of whcih the peak value of the peak 4 of the signal 3 can be determined, which peak value is compared, in a stage 25, with reference value supplied to a reference input 26 and corresponding to the attenuation with the dry gas, the difference therebetween being a measure for the humidity of the gas, which results can be displayed on a display apparatus 27. The threshold circuit 24 can be a multiple threshold circuit or a circuit with a variable threshold value, as has already been remarked above. If required also one of the threshold circuits 14 can be used for this purpose.

It will be clear that FIG. 2 shows only the fundamental structure of a circuit suitable for the present purpose, and that many modifications can be made therein. If a smaller number of magnitudes is to be determined, a corresponding part of this circuit can be left out.

Although, in FIG. 2, separate threshold circuits 14 and counters 16 are shown, it is also possible to store the output signals 3 of the transducers 13 in a memory, and to process then during the time between two successive pulses 1, which allows a simplification of the circuit.

For determining the velocity and direction of the gas flow to be examined, various assemblies of transducers 12 and 13 can be used. In particular transducer pairs with mutually cross directions can be used, and, in a given direction, also measurements in two opposite senses can be used. If the character of the transdsucers is such that they can be used as well as a pulse emitter and a pulse receiver, a measurement in both senses can be obtained by a simple commutation. It is, of course, also possible to use, for a given direction, two pairs, each being intended for one sense of propagation. The number of pairs depends, of course, from the fact whether the direction of the flow factor is to be determined in two or in three dimensions.

FIG. 3 shows, furthermore, a special embodiment of an apparatus suitable for the present purposes. This embodiment comprises a single piezo-electric pulse generator 12 which is arranged at one side of a flow portion to be examined, and in front of this pulse generator 12 a reflection body 28 is arranged which, for the sake of simplicity, is represented as a triangle. The emitted pulses 1 are reflected against the oblique planes 29 of this body 28 towards an associated transducer 13. The acoustic pulses proceed, therefore, through the gas flow first in one and then in the other sense.

If required a symmetrical geometry of the pulse tracks before and after reflection can be obtained by a suitable design of the pulse generator 12 and of the body 28.

In particular the body 28 is made in the form of a three-sided pyramid or tetrahedron, in which case three transducers 13 are to be used, and then an accurate determination of the flow vector 30 can be obtained.

It is also possible to use a larger number of piezo-electric transducers than is required for a direction measurements, in particular if teh flow to be examined can originate from all directions, and, in certain directions, certain transducers or transducer pairs are less favourably situated for obtaining a good transit time measurement. In that case the transducers with the least favourable position can be switched off, and then sufficient transducers remain for obtaining an unambiguous determination of the direction. Switching off can, for instance, take place on the basis of a preceding coarse direction measurement, for instance at the beginning of a measurement series.

Although in the preceding description gas flows have been discussed, it will be clear that also in the case of liquid flows similar measurements can be formed.

For measuring the humidity of a gas also use can be made of less attenuated oscillations, and then the amplitude decay of the envelope is determined.

I claim:

1. Apparatus for determining the velocity and direction of a gas flow comprising:
   first transducer means for emitting a strongly damped acoustic signal characterized by a waveform having one peak of amplitude substantially greater than all other peaks in said waveform;
   second transducer means for receiving said acoustic signal;
   threshold circuit means associated with said second transducer for setting a threshold level and deriving an output signal in response to reception of a peak exceeding said level;
   energizing circuit means for driving said first transducer; and
   timer means connected to said energizing circuit means and an output of said threshold circuit means for measuring the time lapse between said emission and said reception;
   said threshold level being adjustable to a level lower than said one peak but higher than said all other peaks, whereby said output signal is normally triggered if at all only by said one peak to avoid erroneous time measurements.

2. The apparatus of claim 1 wherein said timer means comprises counter means driven by timing pulses generated by a clock circuit, said counter enabled upon said emission and stopped upon said output, said clock circuit being asynchronous with said emission of acoustic signal.

3. The apparatus of claim 2 wherein said acoustic signal is emitted at a repetition rate substantially slower than the decay frequency of said damped acoustic signal and wherein the frequency of said timing pulses is substantially higher than said decay frequency.

4. The apparatus of claim 2 or claim 3 wherein a plurality of said time measurements is performed successively and a transit time between said transducer means is determined by statistical interpolation of said time measurements.

5. The apparatus of claim 3 further comprising summing circuit means and said second transducer means comprise a plurality of second transducers arranged along different direction in relation to said first transducer means, wherein the sum of said transit times measured along said different directions is used for computing the temperature of said flow.

6. The apparatus of claim 2 or claim 5 further comprising means for varying said threshold level thereby to determine the amplitude of said one peak, and comparator circuit means for comparing the amplitude so determined aginst a reference value, whereby the attenuation of said acoustic signal is measured for determining the humidity of said flow.

7. The apparatus of claims 1 wherein said first transducer means comprise a single transducer, said second transducer means comprises a plurality of transducers, further comprising an acoustically reflecting body arranged for reflecting said acoustic signal between said single first transducer and said plurality of transducers along different directions through said flow.

8. The apparatus of claim 7 wherein said reflecting body is a regular pyramid having an apex directed towards said single transducer.

9. The apparatus of claim 2 further comprising first means for determining the direction of said flow based on said time measurements, and wherein the number of said transducers is greater than the minimum required for determining said direction of flow, and second means associated with said first means for selectively disabling those of said transducers least favorably positioned in relation to the direction of flow so determined.

10. A method for determining the velocity and direction of a gas flow by measuring the transit time of an acoustic signal between multiple transducer pairs along a plurality of directions and deriving the velocity and direction of the flow from the difference in said transit time mesurements, comprising the steps of:

generating a clock pulse train;

emitting at one transducer a strongly damped acoustic signal asynchronously with said clock pulse train for inducing a damped alternating electrical output signal in a second transducer, said output signal characterized by a waveform deflection which in one sense has a larger amplitude than all other deflections of said waveform;

comparing said output signal against a threshold value lower than the peak value of said one deflection;

detecting a deflection of said output signal exceeding said threshold value;

counting said clock pulses generated between said emission and said detection thereby to obtain an approximate transit time measurement;

repeating said steps of emitting, comparing, detecting, and counting a statistically sufficient number of times; and averaging the approximate time measurements obtained by each repetition thereby to comput a statistically valid transit time measurement with an accuracy greater than the period of said clock pulses.

11. The method of claim 10 wherein said one deflection is the first deflection of said waveform in said one sense.

12. The method of claim 10 or claim 11 wherein said threshold value is set above the peak value of any deflection of said waveform other than said one deflection such that if said one waveform is attenuated in transit below said threshold value no transit time measurement based on that particular emission is included in said average.

* * * * *